United States Patent [19]
Mottier et al.

[11] Patent Number: 5,318,777
[45] Date of Patent: Jun. 7, 1994

[54] SAL OLEIN, A PROCESS FOR ITS PREPARATION AND COSMETIC COMPOSITIONS CONTAINING IT

[75] Inventors: Line Mottier, Forel; Jean-Louis Viret, Brent; Hans-Juergen Wille, Villeneuve, all of Switzerland

[73] Assignee: Nestec S.A., Vevey, Switzerland

[21] Appl. No.: 642,471

[22] Filed: Jan. 17, 1991

[30] Foreign Application Priority Data

Feb. 12, 1990 [EP] European Pat. Off. ........ 90102667.4

[51] Int. Cl.$^5$ .............................................. A61K 9/107
[52] U.S. Cl. ................. 424/401; 424/195.1; 424/59; 514/783; 514/938
[58] Field of Search ............ 424/401, 195.1, 59; 514/783

[56] References Cited

U.S. PATENT DOCUMENTS 4,534,981  8/1985  Zabotto et al. ............... 424/63

OTHER PUBLICATIONS

English Translation of Japanese Patent 82-127694, annotated by Translator.

*Primary Examiner*—Thurman K. Page
*Assistant Examiner*—Raj Bawa
*Attorney, Agent, or Firm*—Vogt & O'Donnell

[57] ABSTRACT

A sal fat fraction is obtained by dissolving sal fat in hexane at a temperature above 20° C. and cooling the solution to 5° C. to 12° C. The cooled solution is seeded with 0.05% to 0.5% by weight sal stearin and then cooled to a temperature below −5° C. A solid fraction is removed from the solution and hexane is removed from the liquid fraction to obtain a sal fat fraction which has a solid fat content at 20° C. of 0% by weight and a solid fat content at 10° C. below 4.5% by weight.

6 Claims, No Drawings

SAL OLEIN, A PROCESS FOR ITS PREPARATION AND COSMETIC COMPOSITIONS CONTAINING IT

BACKGROUND OF THE INVENTION

This invention relates to a sal olein as a constituent of the oily phase of cosmetic compositions.

Cosmetic compositions in emulsion form contain fats which are capable of providing the desired properties of application to the skin, i.e. essentially softening, lubricating, nourishing and protective properties to keep the skin supple and to protect it against atmospheric aggressions.

Fats of vegetable origin which have been proposed as suitable ingredients of the oily phases include sal fat which comes from stones of the fruit of the tree "*Shorea robusta.*" According to U.S. Pat. No. 4,534,981, for example, sal fat provides above all the required qualities of suppleness of the skin coupled with a softening effect. However, from the point of view of physical properties, this fat has the disadvantage of negatively modifying the crystallization of the oily phase of the emulsions containing it, the effect of which is to shorten their stability as a function of time and, in addition, to give the emulsions a less attractive appearance by reducing their fineness and their lustre.

Processes for the solvent fractionation of sal fat into stearin and olein are already known. For example, published patent application WO 83.00 418 mentions the use of acetone or 2-nitropropane; Japanese patent application JP 81.127,694 related to the fractionation of sal fat with hexane in two stages. The olein obtained by these processes is solid or semi-solid at ambient temperature (approximately 20° C). The problem addressed by the present invention was to provide a fat in the form of sal olein which, while having the cosmetic properties of sal fat, would not have any of its physical properties harmful to the quality of the emulsions.

SUMMARY OF THE INVENTION

Accordingly, the present invention relates to a sal olein which is characterized in that it has a solid fat content at 20° C. of 0% by weight and in that its content of fats solid at 10° C. is below 4.5% by weight.

The present invention also relates to a process for the production of the above-mentioned sal olein, characterized in that:
the sal fat is introduced into n-hexane in a ratio of sal fat to n-hexane of 1:3 to 1:6 by weight:volume at a temperature above 20° C.,
the mixture is cooled to 5°–12° C.,
the mixture thus cooled is seeded with 0.05 to 0.5% by weight sal stearin,
the mixture is slowly stirred while cooling to a temperature below −5° C in steps or progressively and the mixture is kept at that temperature for 1 to 5 h,
a solid fraction is separated at a temperature below −5° C. and a liquid fraction constituting the olein is collected, after which the n-hexane is removed from this liquid fraction.

DETAILED DESCRIPTION OF THE INVENTION

The process according to the invention is preferably carried out using sal fat refined by the usual methods of mucilage removal, neutralization, bleaching and deodorization. It is also possible to use the semi-refined fat, i.e. treated as far as bleaching, and then to deodorize the olein after fractionation.

The fat is then fractionated using n-hexane either in batches or semi-continuously.

The fractionation step comprises dissolving the fat in a sufficient quantity of n-hexane, preferably in a ratio of sal fat to hexane of approximately 1:4 by weight:volume at a temperature in the range from 20° to 60° C. and preferably at a temperature of the order of 20° C.

The solution is then gradually cooled, for example in a thermostatically controlled crystallizer, to the seeding temperature, i.e. preferably to 5° –12° C., with or without stirring.

Alternatively, the sal fat melted, for example, at 40° to 60° C. may be mixed with n-hexane cooled, for example, to a temperature of −5° C. to 0° C.

To obtain controlled crystallization, i.e. to ensure that the crystals are relatively homogeneous, the above solution is seeded with crystals of sal stearin. The crystals in question may initially be obtained by carrying out the process without seeding and thereafter preferably from a preceding batch. The seeding level is from 0.05 to 0.5% and preferably of the order of 0.1% by weight.

The dispersion is then gradually cooled with slow stirring, preferably at a cooling rate of 5 to 10° C./h, to a temperature of the cooling fluid of −7 to −20° C., for example to −9° C., after which this temperature is maintained for 2 to 5 h and preferably for around 4 h with slow stirring.

Dense nodular crystals are formed and may be separated by filtration, for example using a vacuum filtration unit, or even by decantation or centrifugation. The liquid fraction is collected.

The crystals may be washed with n-hexane which has been cooled, preferably to around −10° C., and the washing waters may be collected and combined with the preceding liquid fraction.

The n-hexane is then removed from the liquids containing the olein, for example by evaporation in vacuo. The solvent-free liquids are preferably treated by stripping with steam in vacuo under conditions which do not cause isomerization, preferably under a pressure of 1 to 4 mbar and at a temperature below 220° C., for example of the order of 200° C., to eliminate every trace of n-hexane.

The present invention also relates to a cosmetic composition containing 2 to 80% by weight sal olein.

The cosmetic composition may be aqueous or anhydrous. An aqueous composition according to the invention may be in the form of a water-in-oil or oil-in-water emulsion, the concentration of sal olein preferably being from 4 to 20% by weight. The cosmetic composition may be, for example, a moisturizing or cleansing gel, a milk, a skin-care or sun cream, a tinted foundation. In a composition of this type, the oily phase may contain other animal, vegetable, mineral or synthetic oils. It may also contain waxes, long-chain alcohols, thickeners, gelling agents. When it is in the form of an emulsion, a cosmetic composition contains 1 to 20% by weight of an emulsifier.

In an anhydrous cosmetic composition, the oily phase may contain 10 to 80% by weight and preferably 10 to 40% by weight sal olein, based on the total weight of the composition. In addition, it may contain other oils and a relatively high proportion, for example 5 to 30% by weight, of waxes. For example, it may be in the form of a sunscreen oil (in which case it contains a solar filter to absorb ultraviolet rays), an anhydrous balm, or lipstick.

The compositions according to the invention may also contain various additives, including in particular colourants, perfumes, preservatives, UV filters, nacreous agents and mineral or organic fillers. In one advantageous embodiment, they contain antioxidants in a quantity of 0.02 to 0.2% by weight.

EXAMPLES

The invention is illustrated by the following Examples in which parts and percentages are by weight, unless otherwise indicated.

EXAMPLE 1

A refined sal fat having the following fatty acid composition, as determined by chromatographic analysis of the methyl esters, is used:

|  | % |
|---|---|
| C 16:0 | 5.1 |
| C 18:0 | 43.6 |
| C 18:1 | 39.4 |
| C 18:2 | 1.7 |
| C 18:3α | 0.6 |
| C 20:0 | 7.9 |
| C 20:1 | 1.2 |
| Others | 0.5 |

In a 100 l reactor heated to 52° C., 15 kg sal fat and 60 l n-hexane are mixed while stirring until dissolution is complete. The mixture is then cooled to 8° C., after which 15 g sal stearin obtained in the same way as in this Example, but without seeding, are added. The mixture is then cooled in steps first to 0° C. over a period of 3 h with slow stirring and then to −6° C. over a period of 1 h with slow stirring. The suspension of crystals formed is then filtered using a filter cooled to 0° C. After the crystals have been washed with 10 l n-hexane cooled to −10° C., the washing waters are combined with the filtrate, after which the n-hexane is evaporated from the solution in a rotary vacuum evaporator. 5.16 kg sal olein having the following fatty acid composition, as determined by chromatography, are thus collected:

|  | % |
|---|---|
| C 16:0 | 6.2 |
| C 18:0 | 26.7 |
| C 18:1 | 54.7 |
| C 18:2 | 4.1 |
| C 18:3α | 1.2 |
| C 20:0 | 5.0 |
| C 20:1 | 1.8 |
| Others | 0.3 |

The solid fat content (SFC) is determined from the melting curve of the fat by pulsed NMR (nuclear magnetic resonance of the proton). The solid fat content is the percentage of solid fat present in the fat partly melted at a given temperature. The following results are obtained:

|  | SFC (%) at | |
|---|---|---|
|  | 10° C. | 20° C. |
| Sal fat | 77 | 61 |
| Sal olein | 3 | 0 |

It can be seen that the sal olein obtained in accordance with the invention is completely liquid at the normal storage temperature of around 20° C.

EXAMPLE 2

100 g of the refined sal fat used as starting material in Example 1 are dissolved with slow stirring in 400 ml n-hexane accommodated in a flask. The flask is kept at 20.8° C. After dissolution, the mixture is gradually cooled by keeping the flask in a refrigerating fluid while stirring at 100 r.p.m. A temperature of −9° C. is reached in the refrigerating fluid in 3 h 30. When the temperature has reached 5° C., the solution is seeded with 0.1% sal stearin.

The final temperature of −9° C. is maintained for 2 h with slow stirring, after which the crystals which have appeared are filtered in a Büchner filter cooled to −10° C. After washing with n-hexane cooled to −10° C., the solvent is evaporated in a rotary vacuum evaporator. Sal olein is thus obtained in a yield of 33.8 g, serving as reference in the following comparison Examples.

COMPARATIVE EXAMPLES 1-2

1. For comparison, the same starting material is fractionated
    a) in accordance with Japanese patent application JP 81.127.694
    b) in accordance with Example 1 of published patent application WO 83.00.418.

The SFC, the yield, the appearance at 20° C. and the fatty acid composition of the oleins obtained are shown in Table I below.

TABLE I

| SFC(%) at | Comparison a) | Comparison b) | Reference |
|---|---|---|---|
| 0° C. | 41.5 | 53.6 | 27.5 |
| 10° C. | 14 | 43.6 | 2.7 |
| 20° C. | 1.5 | 21 | 0 |
| 30° C. | 0.2 | 1.8 | 0 |
| Yield (%) | 38.3 | 53.1 | 34.4 |
| Appearance at 20° C. | Semi-solid | Solid | Clear liquid |

| Composition based on principal fatty acids (%) | Comparison a) | Comparison b) | Reference |
|---|---|---|---|
| C 16:0 | 6.7 | 7.5 | 6 |
| C 18:0 | 29.9 | 34.7 | 23.2 |
| C 18:1 | 51.4 | 46.6 | 58.2 |
| C 18:2 | 3.7 | 3 | 5.1 |
| Others | 8.3 | 8.2 | 7.5 |

2. The same sal olein is fractionated with the usual solvents acetone (c) and d)) and isopropanol (e), f) and g)) under optimized conditions. These conditions are shown in Table II below. The SFC at different temperatures and the yield of olein are determined in each case.

TABLE II

| | Fractionation conditions | | | | | | |
|---|---|---|---|---|---|---|---|
| | Fat:solvent | Final tempera- | Time at final temperature | SFC (%) at (°C.) | | | Yield |
| Test | ratio | ture (°C.) | (h) | 0 | 10 | 20 | (%) |
| Reference | 1/4 | −9 | 2 | 33.5 | 3.4 | 0 | 33.1 |
| c) | 1/3 | 0 | 3 | 23.2 | 1.3 | 0.1 | 18 |
| d) | 1/4 | 0 | 3 | 27.2 | 2.4 | 0.5 | 21.1 |
| e) | 1/3 | 4 | 3 | 32.2 | 5.2 | 0.3 | 23.9 |
| f) | 1/3 | 15 | 2 | 32 | 9.4 | 4.1 | 23.3 |

TABLE II-continued

| Test | Fractionation conditions | | | SFC (%) at (°C.) | | | Yield (%) |
|---|---|---|---|---|---|---|---|
| | Fat: solvent ratio | Final temperature (°C.) | Time at final temperature (h) | 0 | 10 | 20 | |
| g) | 1/3 | 10 | 2 | 28.2 | 6.5 | 3.3 | 18.5 |

The results of the Comparison Tests set out in Table I above clearly show that only the olein obtained in accordance with the invention with n-hexane does not lead to the formation of crystals at ambient temperature (SFC 0% at 20° C.). The other solvents typically used in the fractionation of fats (Table II) lead to a lower yield of olein.

EXAMPLES 3–15

These Examples relate to the dermocosmetic application of the sal olein according to the invention. The nomenclature used in these Examples is the nomenclature of the Cosmetic, Toiletry and Fragrance Association, Inc., Washington, D.C. (CTFA)

To prepare the emulsions, the components of the lipid phase A are mixed and heated to 70° C. The aqueous phase B is prepared by mixing its components and heating to 70° C. The lipid phase A is added to the aqueous phase B at 70° C. while stirring at average speed. The mixture of the two phases is homogenized, stirred at 100 r.p.m. and then left to cool to 45–50° C. for the water-in-oil emulsions and to 35–40° C. for the oil-in-water emulsions.

The additives C, if any, are added at that temperature, after which cooling is continued to ambient temperature with slow stirring, stirring being stopped when the product is semi-fluid.

The anhydrous products are obtained in the same way, but without homogenization, by hot mixing and gradual cooling with slow stirring.

3. Cleansing gel (oil in water emulsion)

| | % | |
|---|---|---|
| Lipid phase A | | 20.55 |
| Peg 8 C12–C20 alkyl ester (C12–C20 fatty alcohol esters containing polyoxyethylene and polyglycerol) | 4.0 | |
| Sal olein | 5.0 | |
| 4-Ethyl laurate | 10 | |
| Nonoxynol-10 (polyglycol ether) | 1.5 | |
| Triethylcitrate, butylhydroxyanisole (BHA) and tocopherol | 0.05 | |
| Aqueous phase B | | 74.87 |
| Carbomer 940 (crosslinked acrylic acid polymer in the form of a 2% dispersion in water) | 40 | |
| Water | 34.87 | |
| Additives C | | 4.58 |
| Glucamine, 20% aqueous solution | 4.5 | |
| Methyl chlorothiazolinone and methyl isothiazolinone | 0.08 | |
| | | 100 |

4. Cleansing milk (oil-in-water emulsion)

| | % | |
|---|---|---|
| Lipid phase A | | 21.55 |
| Sal olein | 7 | |
| 2-Ethylhexyl-2-ethyl hexanoate | 3 | |
| C10–18 fatty acid triglyceride | 4 | |
| Paraffin oil | 3 | |
| Glycerol stearate | 3 | |
| Stearic acid | 1.5 | |
| Tocopherol, BHA and triethyl citrate | 0.05 | |
| Aqueous phase B | | 48.07 |
| Water | 47.88 | |
| Tetrahydroxypropyl ethylenediamine | 0.14 | |
| Disodium ethylenediamine tetraacetate (EDTA) | 0.05 | |
| Additives C | | 30.38 |
| Hydroxyethyl cellulose, 2% aqueous solution | 30 | |
| Methyl chlorothiazolinone and methyl isothiazolinone | 0.08 | |
| Perfume | 0.3 | |
| | | 100 |

5. Moisturizing cream (oil-in-water emulsion)

| | % | |
|---|---|---|
| Lipid phase A | | 26.05 |
| Peg 8 C12-C18 alkyl ester (C12–C18 fatty alcohol esters containing polyoxyethylene and polyglycerol) | 10 | |
| Sal olein | 7 | |
| Isodecyl laurate | 5 | |
| Cetoaryl alcohol | 4 | |
| Tocopherol, BHA and triethyl citrate | 0.05 | |
| Aqueous phase B | | 73.87 |
| Water | 62.87 | |
| C12–C18 fatty alcohols containing polyoxyethylene and polyglycerol | 2 | |
| Propylene glycol | 5 | |
| Panthenol | 2 | |
| Sodium PCA | 2 | |
| Additive C | | 0.08 |
| Methyl chlorothiazolinone and methyl isothiazolinone | 0.08 | |
| | | 100 |

6. Cleansing cream (oil-in-water emulsion)

| | % | |
|---|---|---|
| Lipid phase A | | 24.55 |
| Sal olein | 7 | |
| 2-Ethylhexyl-2-ethyl hexanoate | 3 | |
| Steareth-21 (nonionic emulsifier) | 2 | |
| Cetoaryl alcohol | 1 | |
| C10–C18 fatty acid triglyceride | 4 | |
| Paraffin oil | 3 | |
| Glycerol stearate | 3 | |
| Stearic acid | 1.5 | |
| Tocopherol, BHA and triethyl citrate | 0.05 | |
| Aqueous phase B | | 45.07 |
| Water | 44.88 | |
| Tetrahydroxypropyl ethylenediamine | 0.14 | |
| Disodium ethylenediamine tetraacetate (EDTA) | 0.05 | |
| Additives C | | 30.38 |
| Hydroxyethyl cellulose, 2% aqueous dispersion | 30 | |
| Methyl chlorothiazolinone and methylisothiazolinone | 0.08 | |
| Perfume | 0.30 | |
| | | 100 |

7. Collagen milk (oil-in-milk emulsion)

| | % | |
|---|---|---|
| Lipid phase A | | 21.55 |
| Sal olein | 7 | |
| C10–C18 triglyceride | 4 | |

-continued

|  | % |  |
|---|---|---|
| 2-Ethylhexyl-2-ethyl hexanoate | 3 |  |
| Paraffin oil | 3 |  |
| Glycerol stearate | 3 |  |
| Stearic acid | 1.5 |  |
| Tocopherol, triethyl citrate and BHA | 0.05 |  |
| Aqueous phase B |  | 45.07 |
| Water | 43.62 |  |
| Tetrahydroxypropyl ethylenediamine | 1.4 |  |
| Disodium ethylenediamine tetraacetate (EDTA) | 0.05 |  |
| Additives C |  | 33.38 |
| Hydroxyethyl cellulose, 2% aqueous suspension | 30 |  |
| Collagen | 3 |  |
| Methyl chlorothiazolinone and methyl isothiazolinone | 0.08 |  |
| Perfume | 0.30 |  |
|  |  | 100 |

8. Moisturizing milk (oil-in-water emulsion)

|  | % |  |
|---|---|---|
| Lipid phase A |  | 27.05 |
| Isocetoareth-10 stearate | 10 |  |
| Sal olein | 7 |  |
| Isodecyl laurate | 5 |  |
| Cetoaryl alcohol | 2 |  |
| Glycerol stearate | 3 |  |
| Tocopherol, BHA and triethyl citrate | 0.05 |  |
| Aqueous phase B |  | 72.67 |
| Water | 48.67 |  |
| Hydroxyethyl cellulose, 2% aqueous suspension | 20 |  |
| Panthenol | 2 |  |
| Sodium PCA | 2 |  |
| Additives C |  | 0.28 |
| Perfume | 0.1 |  |
| Tetrasodium etidronate | 0.1 |  |
| Methyl chlorothiazolinone and methyl isothiazolinone | 0.08 |  |
|  |  | 100 |

9. Tinted moisturizing emulsion (tinted foundation, oil-in-water)

|  | % |  |
|---|---|---|
| Lipid phase A |  | 18.95 |
| Isoceteth-10-stearate and isocetoareth-10 stearate | 7 |  |
| Sal olein | 4.9 |  |
| Isodecyl laurate | 3.5 |  |
| Cetoaryl alcohol | 1.4 |  |
| Glycerol stearate | 2.1 |  |
| Tocopherol, BHA and triethyl citrate | 0.05 |  |
| Aqueous phase B |  | 50.77 |
| Water | 32.77 |  |
| Hydroxyethyl cellulose, 2% aqueous suspension | 14 |  |
| Panthenol | 2 |  |
| Sodium PCA | 2 |  |
| Additives C |  | 30.28 |
| Concentrated pigments |  |  |
| white | 22.7 |  |
| yellow | 4.8 |  |
| red | 1.5 |  |
| brown to 40% pigment, remainder glycerol, sorbitol and polysorbate 20 | 1 |  |
| Perfume | 0.1 |  |
| Tetrasodium etidronate | 0.1 |  |
| Methyl chlorothiazolinone and methyl isothiazolinone | 0.08 |  |

-continued

|  | % |  |
|---|---|---|
|  |  | 100 |

10. Skin-care cream (water-in-oil emulsion)

|  | % |  |
|---|---|---|
| Lipid phase A |  | 39 |
| Peg-1 glycerol sorbitan oleo-stearate and paraffin wax | 12 |  |
| Paraffin oil | 13 |  |
| Sal olein | 8 |  |
| Caprylic and capric acid triglycerides | 5 |  |
| 2-Phenoxyethanol, methyl parabene, ethyl parabene, propyl parabene and butyl parabene | 1 |  |
| Aqueous phase B |  | 61 |
| Water | 58.3 |  |
| Magnesium sulfate heptahydrate | 0.7 |  |
| Glycerol | 2 |  |
|  |  | 100 |

11. Sun cream (water-in-oil emulsion)

|  | % |  |
|---|---|---|
| Lipid phase A | 39 | 39 |
| Peg-1 glycerol sorbitan oleo-stearate and paraffin wax | 12 |  |
| Paraffin oil | 11 |  |
| Sal olein | 8 |  |
| Caprylic and capric acid triglycerides | 5 |  |
| Octyl methoxycinnamate | 2 |  |
| 2-Phenoxyethanol, methyl parabene, ethyl parabene, propyl parabene and butyl parabene | 1 |  |
| Aqueous phase B |  | 61 |
| Water | 58.3 |  |
| Magnesium sulfate heptahydrate | 0.7 |  |
| Glycerol | 2 |  |
|  |  | 100 |

12. Oil for the face and body (anhydrous)

|  | % |
|---|---|
| Paraffin oil | 56.85 |
| Sal olein | 10 |
| Octyl octanoate | 10 |
| C10–C18 triglycerides | 10 |
| Silicone oil | 5 |
| Isodecyl laurate | 5 |
| Octyl methoxycinnamate | 3 |
| Perfume | 0.1 |
| Tocopherol, triethyl citrate and BHA | 0.05 |
|  | 100 |

13. Anhydrous balm

|  | % |
|---|---|
| Paraffin | 4 |
| Ozocerite | 5 |
| 2-Ethylhexyl-2-ethyl hexanoate | 45.6 |
| Sal olein | 40 |
| Isodecyl laurate | 5 |
| Antioxidant | 0.1 |
| Perfume | 0.3 |
|  | 100 |

14. Anhydrous cleansing gel

|  | % |
|---|---|
| Paraffin oil | 45.6 |
| Sal olein | 30 |
| 2-Ethylhexyl-2-ethyl hexanoate | 10 |

| -continued | % |
|---|---|
| Isodecyl laurate | 5 |
| Ozocerite | 5 |
| Paraffin | 4 |
| Tocopherol, BHA and triethyl citrate | 0.1 |
| Perfume | 0.3 |
| | 100 |
| 15. Lipstick (anhydrous) | |
| Castor oil | 27.45 |
| Isopropyl myristate | 20 |
| Sal olein | 10.5 |
| Beeswax | 10.5 |
| Candelilla wax | 7.5 |
| Ozocerite | 5.5 |
| Isopropyl lanolate | 5 |
| Colourants | 13.55 |
| | 100 |

All the cosmetic products of Examples 3 to 15 were tested and show high stability over a period of 3 months at 20° C., 37° C. and 47° C.

They have good organoleptic properties. In other words, both the emulsions and the anhydrous products are homogeneous, fine, smooth and lustrous;

they spread well on the skin and show good cutaneous penetration. The skin has a pleasant feel and is smooth, soft and silky.

During production, during the tests and during the physicochemical analyses, there was no crystallization of the lipid phase containing the olein whereas the use of sal fat leads to stability problems caused by crystallization.

We claim:

1. A sal fat fraction which has a solid fat content at 20° C. of 0% weight and a solid fat content at 10° C. below 4.5% by weight.

2. A cosmetic composition comprising an oily phase which contains a sal fat fraction having a solid fat content at 20° C. of 0% by weight and a solid fat content at 10° C. below 4.5% by weight.

3. A cosmetic composition according to claim 2 wherein the sal fat fraction is present in the composition in an amount of 2% to 80% based on a weight of the composition.

4. A cosmetic composition according to claim 2 wherein the composition is in the form of an emulsion and contains from 4% to 20% by weight sal fat fraction and from 1% to 20% by weight of an emulsifier based on a weight of the emulsion.

5. A cosmetic composition according to claim 2 wherein the composition is in an anhydrous form and wherein the oily phase contains from 10% to 80% by weight sal fat fraction.

6. A cosmetic composition according to claim 2 further comprising 0.02% to 0.2% by weight of an antioxidant based on a weight of the composition.

* * * * *

UNITED STATES PATENT AND TRADEMARK OFFICE
CERTIFICATE OF CORRECTION

PATENT NO. : 5,318,777
DATED : June 7, 1994
INVENTOR(S) : Line Mottier, et al

It is certified that error appears in the above-indentified patent and that said Letters Patent is hereby corrected as shown below:

Column 10, line 6, (line 2 of claim 1), after "0%", insert --by --.

Signed and Sealed this

Sixth Day of September, 1994

Attest:

BRUCE LEHMAN

*Attesting Officer*     *Commissioner of Patents and Trademarks*